United States Patent [19]

Quinlan

[11] 4,088,574
[45] May 9, 1978

[54] EMPLOYING METHYLENE PHOSPHONATES OF OXYALKYLATED POLYALKYLENE POLYAMINES IN CHELATION AND/OR SCALE INHIBITION

[75] Inventor: Patrick M. Quinlan, Webster Groves, Mo.

[73] Assignee: Petrolite Corporation, St. Louis, Mo.

[21] Appl. No.: 744,821

[22] Filed: Nov. 24, 1976

Related U.S. Application Data

[60] Division of Ser. No. 455,344, Mar. 27, 1974, Pat. No. 4,012,440, which is a continuation of Ser. No. 90,837, Nov. 18, 1970, abandoned.

[51] Int. Cl.$^2$ .................................................. C02B 5/06
[52] U.S. Cl. ................................ 210/58; 252/8.55 D; 252/180
[58] Field of Search ................. 21/2.74; 210/54, 58, 210/59; 252/8.55 D, 180; 260/501.12, 502.5

[56] References Cited

U.S. PATENT DOCUMENTS

| | | | |
|---|---|---|---|
| 2,599,807 | 6/1952 | Bersworth | 260/502.5 |
| 2,673,213 | 3/1954 | Bersworth | 260/502.5 |
| 2,917,528 | 12/1959 | Ramsey et al. | 260/502.5 |
| 2,964,549 | 12/1960 | Ramsey et al. | 260/502.5 |
| 3,288,846 | 11/1966 | Irani et al. | 260/502.5 |
| 3,617,578 | 11/1971 | Stanford | 210/58 |
| 3,799,893 | 3/1974 | Quinlan | 252/180 |
| 3,836,462 | 9/1974 | Larsen | 210/58 |

*Primary Examiner*—Charles N. Hart
*Assistant Examiner*—Peter A. Hruskoci
*Attorney, Agent, or Firm*—Sidney B. Ring; Hyman F. Glass

[57] ABSTRACT

Methylene phosphonates of oxyalkylated polyalkylene polyamines having at least three nitrogen atoms wherein there are nitrogen-bonded methylene phosphonate units of the formula — $CH_2PO(OM)_2$. These compounds are used as scale inhibitors, chelating agents, etc.

9 Claims, No Drawings

EMPLOYING METHYLENE PHOSPHONATES OF OXYALKYLATED POLYALKYLENE POLYAMINES IN CHELATION AND/OR SCALE INHIBITION

This Application is a division of Ser. No. 455,344 filed Mar. 27, 1974 now U.S. Pat. No. 4,012,440, granted Mar. 15, 1977, which is a continuation of my copending application Ser. No. 90,837, filed on Nov. 18, 1970, for Methylene Phosphonates of Oxyalkylated Polyalkylene Polyamines and Uses Therefor (now abandoned).

Also copending with this Application, or its parent application Ser. No. 455,344 or Ser. No. 90,837, are my following applications:

Ser. No. 113,092, filed on Feb. 5, 1971 (now abandoned), for Methylene Phosphonates of Amino-Terminated Oxyalkylates and Uses Therefor;

Ser. No. 129,955, filed on Mar. 31, 1971, for Methylene Phosphonates of Glycidyl Reacted Polyalkylene Polyamines and Uses Therefor (now U.S. Pat. No. 3,799,893 granted on Mar. 26, 1974);

Ser. No. 148,216, filed on May 28, 1971, for Methylene Phosphonates of Polydiepoxidized Polyalkylene Polyamines and Uses Therefor, now U.S. Pat. No. 4,035,412, granted July 12, 1977;

Ser. No. 679,389 filed Apr. 22, 1976, which is a continuation of Ser. No. 160,106, filed on July 6, 1971 (now abandoned), for Methylene Phosphonates of Polymerized Polyalkylene Polyamines and Uses Therefor;

Ser. No. 237,883, filed on Mar. 24, 1972, for Polyquaternary Ammonium Methylene Phosphonates and Uses Thereof (now U.S. Pat. No. 3,792,084, granted on Feb. 12, 1974);

Ser. No. 410,714, filed on Oct. 29, 1973 (which is a Division of Ser. No. 237,883) for Use of Polyquaternary Ammonium Methylene Phosphonates to Chelate or Inhibit Formation of Scale, now U.S. Pat. No. 3,867,286 granted on Feb. 18, 1975;

Ser. No. 410,492, filed on Oct. 29, 1973 (which is a Division of Ser. No. 237,883) for Polyquaternary Ammonium Methylene Phosphonates;

Ser. No. 412,603, filed on Nov. 5, 1973 (which is a Division of Ser. No. 237,883) for Use of Polyquaternary Ammonium Methylene Phosphonates in Chelating or Scale Inhibition, now U.S. Pat. No. 3,966,630 granted on June 29, 1976;

Ser. No. 414,946, filed on Nov. 12, 1973, for Use of Polyquaternary Ammonium Methylene Phosphonates as Microbiocides;

Ser. No. 423,671 filed Dec. 11, 1973, now U.S. Pat. No. 3,926,801 granted Dec. 16, 1975 for Methylene Phosphonates of Glycidyl Reacted Polyalkylene Polyamines and Use in Scale and Chelation which is a Division of Ser. No. 129,955 filed Mar. 31, 1971 (now U.S. Pat. No. 3,799,893 granted on Mar. 26, 1974);

Ser. No. 732,562 filed Oct. 15, 1976 (which is a Continuation of Ser. No. 113,092 filed Feb. 5, 1971) for Methylene Phosphonates of Amino-Terminated Oxyalkylates and Uses Therefor.

This invention relates to methylene phosphonates of oxyalkylated polyalkylene polyamines having at least three nitrogen atoms, said methylene phosphonates having nitrogen-bonded methylene phosphonate units of the formula $-CH_2PO(OM)_2$, with M being hydrogen, alkali metal, alkaline earth metal, alkyl ammonium or ammonium, and also to processes of inhibiting scale and chelation.

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating of sequestering agents, so that the solubility of their reaction products is not exceeded. Generally, this approach requires many times as much chelating or sequestering agent as cation present, and the use of large amounts of treating agent is seldom desirable or economical.

More than twenty-five years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity of a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which threshold active compounds sequester the cations of relatively insoluble compounds and the low concentrations at which they act as threshold inhibitors. Therefore, one could also define "threshold" concentrations as all concentrations of threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

A compound that has sequestering powers does not predictably have threshold inhibiting properties. For example, ethylene diamine tetracetic acid salts are powerful sequesterants but have no threshold activities.

In the prior art are such patents as those of Ralston (3,336,221) and Ralston (3,434,969). Ralston (3,336,221) discloses methylene phosphonates of oxyalkylated amines where one —CH$_2$CH$_2$OH group is or two —CH$_2$CH$_2$OH are present when the phosphonate is a monoamine methylene phosphonate and wherein no —CH$_2$CH$_2$OH group or one —CH$_2$CH$_2$OH group is present when the phosphonate is a diamino methylene phosphonate. That Ralston patent does not even suggest any methylene phosphonates of oxyalkylated polyalkylene polyamine having at least three nitrogen atoms. Ralston (U.S. Pat. No. 3,434,969) does not even suggest any methylene phosphonates of oxyalkylated polyamines having at least three nitrogen atoms and discloses only methylene phosphonates of polyalkylene polyamines having 3 to 15 amine groups.

I have now discovered methylene phosphonates of oxyalkylated polyalkylene polyamines having at least three amino units, a process for inhibiting scale such as calcium, barium and magnesium carbonate, sulfate, silicate, etc. scale which comprises employing threshold amounts of said methylene phosphonates of oxyalkylated polyalkylene polyamines having at least three amino units.

The amines employed herein are polyalkylene polyamines, for example, of the formula $$NH_2 \left( A - \underset{H}{N} \right)_n H$$

where $n$ is an integer for example 2 to 25 or more, such as 2-10, but preferably 2-5, etc., and A is an alkylene group —(CH$_2$)$_m$ where $m$ is 2-10 or more, but preferably ethylene or propylene.

One or more of the hydrogen on the CH$_2$ group may be substituted for example, by such groups as alkyl groups, for example, methyl, ethyl, etc. Examples of A include

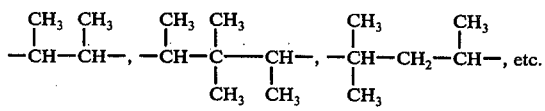

Examples of polyamines include the following: diethylene triamine, dipropylene triamine, triethylene tetramine, tripropylene tetramine, tetraethylene pentamine, tetrapropylene pentamine, polyalkyleneimines, i.e. the higher molecular weight amines derived from alkyleneimine such as polyethyleneimines, polypropyleneimines, for example having 50, 100 or more alkylene amino units, etc. Mixtures of the above polyamine amines and those polyamines containing both ethylene and propylene groups, for example

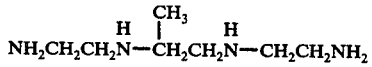

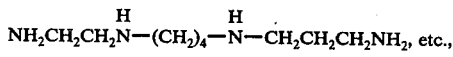

can be employed.

These include the following:

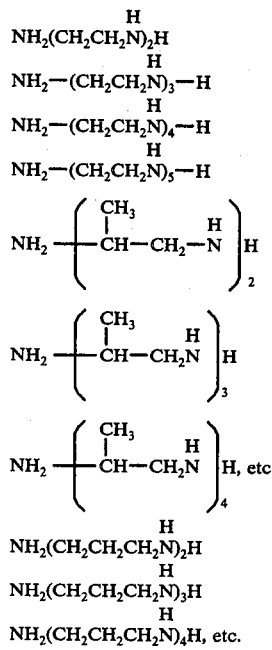

The polyalkylenepolyamines are oxyalkylated with an alkylene oxide of the general formula

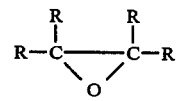

where the R's, which may be the same or different, are hydrogen or a substituted group, preferably alkyl. Examples include ethylene oxide, propylene oxide, butylene oxide, octylene oxide, styrene oxide, cyclohexene oxide, etc. More than one oxide can also be employed such as ethylene and propylene, etc., either added as mixtures or sequentially.

The amount of alkylene oxide added will depend on the particular polyamine oxyalkylated, the number of methylene phosphonates desired in the final product, the system in which it is employed, etc. In general, less than all of the nitrogen-bonded hydrogens are oxyalkylated so as to leave hydrogens which are capable of being phosphomethylolated. Oxyalkylation is carried out in the conventional manner.

The oxyalkylated polyalkylene polyamine is then phosphomethylolated. This is preferably carried out by the Mannich reaction as illustrated in the following reaction where —NH indicates at least one reactive group on the polyamine

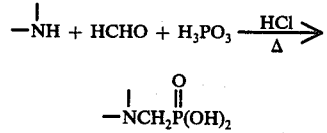

The Mannich reaction is quite exothermic and initial cooling will generally be required. Once the reaction is well under way, heat may be required to maintain refluxing conditions. While the reaction will proceed at temperatures over a wide range, i.e., from 80° to 150° C., it is preferred that the temperatures of the reaction medium be maintained at the refluxing temperatures. The reaction is preferably conducted at atmospheric pressure, although sub-atmospheric and superatmospheric pressures may be utilized if desired. Reaction times will vary, depending upon a number of variables, but the preferred reaction time is 1 to 5 hours, and the most preferred reaction time is 2 ½ to 3 ½ hours.

Although the phosphonic acid or the formaldehyde may be added in either order, or together to the reaction mixture, it is preferred to add the phosphonic acid to the polyamine and then to slowly add the formaldehyde under refluxing conditions. Generally, about ½ to 10 moles or more of formaldehyde and about ½ to 10 moles or more of phosphonic acid can be used per mole equivalent of amine, although the most preferred molar equivalent ratios of formaldehyde: phosphonic acid: amine is 1:1:1. Excess formaldehyde and/or phosphonic acid function essentially as solvents, and thus there is no real upper limit on the amount of these materials which may be used, per mole equivalent of amine, although such excess amounts naturally add to the cost of the final product and are therefore not preferred. The preferred molar equivalent ratios are ½ to 2 moles each of the formaldehyde and phosphonic acid per mole equivalent of amine.

The Mannich reaction will proceed in the presence or the absence of solvents. The reaction may be carried out as a liquid-phase reaction in the absence of solvents or diluents, but is preferred that the reaction be carried out in an aqueous solution containing from about 40 to about 50% of the reaction monomers. Preferred conditions for the Mannich reaction include the use of formaldehyde based on the molar equivalent amount of the amine compound, the use of a stoichiometric amount of phosphonic acid based on the molar equivalent amount of amine (e.g., on the amine active hydrogen content), refluxing conditions and a pH of less than 2 and preferably less than 1.

Although formaldehyde is preferred, other aldehydes or ketones may be employed in place of formaldehyde such as those of the formula

where R + R' are hydrogen, or a hydrocarbon group such as alkyl, i.e. methyl, ethyl, propyl, butyl, etc., aryl, i.e. phenyl, alkylphenyl, phenalkyl, etc., cycloalkyl i.e. cyclohexyl, etc.

The compound can also be prepared by a modified Mannich reaction by employing a chloromethylene phosphonate

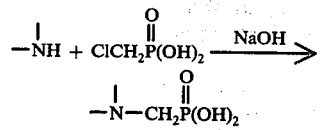

Thus, the compositions of this invention are prepared by
(1) oxyalkylating the alkylene polyamine to the desired degree of oxyalkylation while leaving some unreacted NH groups.
(2) phosphomethylolating the oxyalkylated polyamine so that at least one, or all of the NH groups, or less than all of the groups are phosphomethylolated.

The final reaction product may be summarized by the following idealized formula:

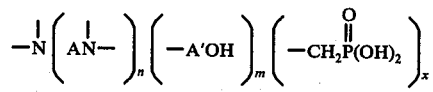

where $n$ is 2–25, $m + x$ equals the sum of the valences on the polyamine (i.e. $n + 2$) with the proviso each has a value of at least one. Where less than all of the nitrogen-bonded hydrogens are reacted either by oxyalkylation or phosphomethylolating they will remain as hydrogen atoms.

In general it is preferred that at least 50% of the nitrogen-bonded hydrogens of the polyamine be replaced by methylene phosphonate groups and the remainder of the nitrogen-bonded hydrogens being oxyalkylated, preferably with one alkylene oxide per hydrogen. Or stated another way by the formula $$R_2N(AN)_nR$$

where the R's are —A'—OH

where at least 50% of the R groups are

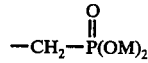

where $n$, $A$ and $A'$ have the meanings stated herein i.e. $n$–2–25, but preferably 2–5, $A'$ is alkylene preferably ethylene, and $M$ is hydrogen or a salt moiety.

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 p.p.m., and are preferably used in concentrations of less than 25 p.p.m.

The compounds of the present invention (e.g. the acid form of the compounds) may be readily converted into the corresponding alkali metal, ammonium or alkaline earth metal salts by replacing at least half of the hydrogen ions in the phosphonic acid group with the appropriate ions, such as the potassium ion or ammonium or alkyl ammonium or with alkaline earth metal ions which may be converted into the corresponding sodium salt by the addition of sodium hydroxide. If the pH of the amine compound is adjusted to 7.0 by the addition of caustic soda, about one half of the —OH radicals on the phosphorous atoms will be converted into the sodium salt form.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 p.p.m. to about 50,000 p.p.m. of scale-forming salts. The compounds of the present invention effectively inhibit scale formation when present in an amount of from 0.1 to about 100 p.p.m., and preferably 0.2 to 25 p.p.m. wherein the amounts of the inhibitor are based upon the total aqueous system. There does not appear to be a concentration below which the compounds of the present invention are totally ineffective. A very small amount of the scale ihibitor is effective to a correspondingly limited degree, and the threshold effect is obtained with less than 0.1 p.p.m. There is no reason to believe that this is the minimum effective concentration. The scale inhibitors of the present invention are effective in both brine, such as sea water, and acid solutions.

In the specific examples the general method of phosphomethylolation is that disclosed in Netherlands Patent 6407908 and 6505237 and in the Journal of Organic Chemistry, Vol. 31, No. 5, 1603–1607 (May, 1966). These references are hereby incorporated by reference.

In general, the method consists of the following: The oxyalkylated polyamine is slowly added with cooling to the mixture of phosphonic and hydrochloric acids. After the addition is completed, the reaction mixture is heated to 100°–110° C. and the aqueous formaldehyde is slowly added over a period of 1 to 1½ hours while maintaining a temperature of 100°–100°. After the addition is completed, the reaction mixture is held at reflux temperatures for 1-2 additional hours. The preferred molar equivalent ratios are ½ – 2 moles each of the formaldehyde and phosphonic acid per mole equivalent of amine, although the most preferred molar equivalent ratios of formaldehyde: phosphonic acid: amine is 1:1:1.

The preferred amine reactants to be used in the preparation of the amino methylene phosphonic acids of the present invention are essentially oxyalkylated polyamines. These amines are easily prepared by the reaction of an alkylene oxide, with heat and pressure in an autoclave, with the desired polyamine. No catalyst is used with the result that hydroxyalkyl polyamines are predominantly formed. Suitable polyamines include the following: diethylene triamine, triethylene tetramine, tetraethylene pentamine, pentaethylene hexamine, ditetramethylene triamine, tritetramethylene tetramine, dihexamethylene triamine and the like. Linear polyamine mixtures that may be oxyalkylated are Amine E-100 from Dow Chemical Company, Amine #1 from Jefferson Chemical Company, and Amine #248 from E. I. DuPont and Company, are also desirable from an economic standpoint. Other suitable amines are polyethyleneimines such as the "PEI" series from Dow Chemical.

The preparation of the oxyalkylated methylene phosphonic acids of this invention is illustrated in the following examples.

EXAMPLE 1

A quantity of 46 g. (0.2 moles) of tetraethylene pentamine that had been ethoxylated with 0.22 wts, (1 mole) of ethylene oxide was dissolved in 140 g. of concentrated HCl and an 80% aqueous solution of 97.2 g. (1.2 moles) of phosphonic acid. Cooling was necessary in order to keep the reaction temperature below 60° C. The resulting solution was heated to reflux temperatures (100°–110° C.) and 107 g. (1.32 moles) of a 37% aqueous formaldehyde solution was added dropwise over a period of 1 hour. After the addition was completed, the reaction mixture was kept at reflux temperature for two additional hours. Ethanol precipitated a yellow solid from the concentrated reaction solution. The solid was dried in a vacuum over for 24 hours at 100° C. An analysis indicated it had a molecular weight of 770 (titration), a nitrogen content of 8.3%, and a phosphorus content of 22.4%, as compared to the calculated values for $C_{16}H_{46}N_5O_{19}P_6$ of 798 (mol. wt.), 8.8% N, 23.3% P.

The sodium salt, when isolated from the reaction mixture, was a hydroscopic solid.

EXAMPLE 2

In a similar manner, 55.2 g. (0.2 moles) of tetraethylene pentamine that had been reacted with 0.46 wts. (2 mole) of ethylene oxide, 82 g. (1 mole) of phosphonic acid, and 89 g. (1.1 mole) of a 37% aqueous solution of formaldehyde, were reacted together to give a phosphonic acid with the following analytical results for $C_{17}H_{48}N_5O_{17}P_5$.

Molecular weight by titration: 730
% N = 8.8
% P = 20.9
Calculated values:
Mol. Wt. = 759
% N = 9.2
% P = 21.7

EXAMPLE 3

In a similar manner, 44.1 g. (0.3 moles) of diethylene triamine that had been ethoxylated with 0.42 wts. (1 mole) of ethylene oxide, 98.4 g. (1.2 moles) of phosphonic acid, and 107 g. (1.32 moles) of a 37% aqueous solution of formaldehyde were reacted together to give a product with the following analytical results for $C_{10}H_{30}N_3O_{13}P_4$.

Mol. Wt. by titration: 519
% N = 7.9
% P = 23.3
Calculated values:
Mol. Wt. = 524
% N = 8.1

% P = 23.7

EXAMPLE 4

In a similar manner, 49.8 g. of Amine #1* that had been reacted with 0.36 wts. of ethylene oxide, 99.6 g. of phosphonic acid, and 107 g. of 37% aqueous formaldehyde solution were reacted together to give a phosphonic acid.

*Amine # 1 consists of 55 – 65% diethylene triamine, 26–33% triethylene tetra-amine, and 8–11% of tetraethylene pentamine plus smaller amounts of higher polyamines.

EXAMPLE 5

Utilizing the method employed in Example I, 57.3 g. (0.3 moles) of diethylene triamine that had been reacted with two moles of ethylene oxide, 74.7 g. (0.9 moles) of phosphonic acid, and 81 g. (1.0 moles) of 37% aqueous formaldehyde, were reacted together to give a phosphonic acid. The analytical results for $C_{11}H_{32}N_3O_{11}P_3$.

Mol. Wt. by Titration: 460
% N = 8.3
% P = 18.8

Calculated values:
Mol. Wt.: 475
% N = 8.8
% P = 19.5

Table I illustrates further examples of N-hydroxyalkyl polyamines that have been utilized in the previous reaction.

TABLE I

| | Polyamine | (Moles) of Oxide Added to each mole of Polyamine |
|---|---|---|
| Example 6 | TEPA* | (1.8) Ethylene oxide |
| Example 7 | TEPA | (2.5) Ethylene oxide |
| Example 8 | TEPA | (3.0) Ethylene oxide |
| Example 9 | TEPA | (3.4) Ethylene oxide |
| Example 10 | TEPA | (4.0) Ethylene oxide |
| Example 11 | TEPA | (1.0) Propylene oxide |
| Example 12 | TEPA | (2.0) Propylene oxide |
| Example 13 | TEPA | (3.0) Propylene oxide |
| Example 14 | DETA** | (2.0) Ethylene oxide |
| Example 15 | DETA | (2.5) Ethylene oxide |
| Example 16 | DETA | (1.0) Propylene oxide |
| Example 17 | DETA | (1.5) Propylene oxide |
| Example 18 | DETA | (2.0) Propylene oxide |
| Example 19 | TETA | (1.0) Ethylene oxide |
| Example 20 | TETA*** | (2.0) Ethylene oxide |
| Example 21 | TETA | (2.5) Ethylene oxide |
| Example 22 | TETA | (2.0) Propylene oxide |
| Example 23 | TETA | (1.0) Butylene oxide |
| Example 24 | PEHA**** | (1.0) Ethylene oxide |

*Tetraethylene pentamine (TEPA)
**Diethylene triamine (DETA)
***Triethylene tetramine (TETA)
****Pentaethylene hexamine (PEHA)

The compounds of this invention may also be prepared in hot, alkaline, aqueous solution by the reaction of chloromethylene phosphonic acid with the oxyalkylated polyamines.

This method has been described by Bersworth in U.S. Pat. Nos. 2,599,807 and 2,841,611 and by Ramsey in U.S. Pat. No. 2,917,528.

In carrying out the reaction sufficient alkalinity must be present to neutralize the acidity of the chloromethyl phosphonic acid and absorb the hydrochloric acid liberated by the reaction. It is desirable to maintain an excess of the alkaline material, such as sodium hydroxide, to drive the reaction to completion.

One or more or all of the remaining hydrogen atoms on the nitrogen atoms in the oxyalkylated polyamines may be replaced with methylene-phosphonic groups depending on the proportions of the oxyalkylated polyamine and the chloromethylene phosphonic acid reactants. Since the reaction products are obtained in the form of salts, depending on the neutralizing base used, they may be converted to the free acids by reaction with inorganic acids or ion exchange resins.

EXAMPLE 25

46 g. (0.2 moles) of the reaction product of tetraethylene pentamine with 0.22 wts. (1 mole) of ethylene oxide is dissolved in 200 ml. of water and 0.6 moles of sodium hydroxide (30% aqueous solution) are added with cooling. The solution is heated to reflux and stirred while 1.2 moles NaOH (30% aqueous solution) and 156.6 g. (1.2 moles) of chloromethylene phosphonic acid are added simultaneously from two addition funnels. The addition requires 2-3 hours, and the resulting solution is refluxed overnight. The resulting sodium salt may be isolated by concentration of the solution under reduced pressure, and filtering off the sodium chloride.

EXAMPLE 26

In a similar manner 44.1 (0.3 moles) of the reaction product of diethylene triamine with 0.42 wts. (1 mole) of ethylene oxide was reacted with 156.6 g. (1.2 moles) of chloromethylene phosphonic acid.

The degree of phosphomethylolation can be controlled by varying the molar ratios of the reactants. However, for effective scale inhibition, I have found that the maximum degree of phosphomethylolation, (100%) is to be preferred. In other words, a complete replacement of the remaining active hydrogen atoms on the N-hydroxyalkyl substituted alkylene polyamines by methylene phosphonate groups has been found to be most desirable for scale inhibition.

These methylene phosphonates are threshold active scale inhibitors at room temperaure, and are also effective at elevated temperatures. They also retain their effectiveness in acid and salt solution and have excellent solubility in waters with high hardness content.

CALCIUM SCALE INHIBITION TEST

The procedure utilized to determine the effectiveness of my scale inhibitors in regard to calcium scale is as follows:

Several 50 ml. samples of a 0.04 sodium bicarbonate solution are placed in 100 ml. bottles. To these solution is added the inhibitor in various known concentrations. 50 ml. samples of a 0.02 M $CaCl_2$ solution are then added.

A total hardness determination is then made on the 50—50 mixture utilizing the well known Schwarzenbach titration. The samples are placed in a water bath and heated at 180° F. 10 ml. samples are taken from each bottle at 2 and 4 hour periods. These samples are filtered through millipore filters and the total hardness of the filtrates are determined by titration.

$$\frac{\text{Total hardness after heating}}{\text{Total hardness before heating}} \times 100 = \% \text{ inhibition}$$

Table II describes the scale inhibition test results that I have obtained. In the table "n" defines n as it appears in Formula above it.

Amine E-100 (Dow) is TEPA 10%, PEHA 40%, cyclic amines 20%, branched amines 20%, polymers (chains having more than 5 ethyleneamine groups 10%).

TABLE II

INHIBITIONS OF SCALE FORMATION FROM A $Ca\ CO_3$ SOLUTION AT 180°F. FOR 4 HOURS

| Methylene phosphonated N-hydroxyalkyl ethylene polyamine inhibitor | Salt | $H_2N(CH_{2_n}CH_2N)_nH$ | Conc. ppm | % Scale Inhibition |
|---|---|---|---|---|
| Pentamine + 1 mole EtO | H | 4 | 50 | 64 |
| Pentamine + 1 mole EtO | H | 4 | 20 | 45 |
| Pentamine + 1 mole EtO | Na | 4 | 50 | 54 |
| Pentamine + 1 mole EtO | Na | 4 | 20 | 38 |
| Pentamine + 2 moles EtO | H | 4 | 50 | 62 |
| Pentamine +2 moles EtO | H | 4 | 20 | 45 |
| Pentamine + 2 moles EtO | Na | 4 | 50 | 49 |
| Pentamine + 2 moles EtO | Na | 4 | 20 | 36 |
| Pentamine + 3 moles EtO | H | 4 | 50 | 57 |
| Pentamine + 3 moles EtO | H | 4 | 20 | 46 |
| Pentamine + 3 moles Eto | Na | 4 | 50 | 58 |
| Pentamine + 3 moles EtO | Na | 4 | 20 | 39 |
| Triamine + 1 mole EtO | H | 2 | 50 | 68 |
| Triamine + 1 mmole EtO | H | 2 | 20 | 57 |
| Triamine + 1 mole EtO | Na | 2 | 50 | 60 |
| Triamine + 1 mole EtO | Na | 2 | 20 | 53 |
| Triamine + 2 moles EtO | H | 2 | 50 | 67 |
| Triamine + 2 moles EtO | H | 2 | 20 | 56 |
| Triamine + 2 moles EtO | Na | 2 | 50 | 64 |
| Triamine + 2 moles EtO | Na | 2 | 20 | 51 |
| Amine #1 + mole EtO | H | 2.5 | 50 | 54 |
| Amine #1 + 1 mole Eto | H | 2.5 | 20 | 47 |
| Amine #1 + 1 mole EtO | Na | 2.5 | 50 | 61 |
| Amine #1 + 1 mole EtO | Na | 2.5 | 20 | 45 |
| Amine E-100 + 2 moles EtO | H | | 50 | 81 |
| Amine E-100 + 2 moles EtO | H | | 20 | 62 |
| Amine E-100 + 2 moles EtO | Na | | 50 | 68 |
| Amine E-100 + 2 moles EtO | Na | | 20 | 47 |
| Commercial organic phosphate inhibitor | — | — | 50 | 40 |
| | | | 20 | 35 |
| Commercial organic phosphonate inhibitor | Na | | 50 | 42 |
| Commercial organic phosphonate inhibitor | Na | | 20 | 35 |

USE IN THE CHELATION OR SEQUESTRATION OF METAL IONS

The chelating or sequestering agents of the present invention are of wide utility such as when it becomes necessary to sequester or inhibit the precipitation of metal cations from aqueous solutions. Among their many uses are the following applications:

Soaps and detergents, textile processing, metal cleaning and scale removal, metal finishing and plating, rubber and plastics, industry, pulp and paper industry, oil-well treatment, chelation in biological systems.

When oxyalkylated, oxyalkyl groups, particularly hydroxyethyl or hydroxypropyl, etc. groups, are incorporated into the amino methylene phosphonic acids of this invention, this enhances their effectiveness in sequestering $Fe^{+3}$. Because they form stable chelates with ferrous ion as well as other metal ions, they are also suitable for other purposes.

An important function of these compounds is their ability to sequester $Fe^{+2}$. In secondary oil recovery by means of water floods, waters are frequently mixed on the surface prior to injection. Frequently these waters contain amounts of $Fe^{+2}$ and $H_2S$. If these incompatible waters are mixed, an FeS precipitate results which can plug the sand face of the injection well. Another of their functions is to prevent formation of gelatinous iron hydroxides in the well and in the effluent production waters.

To demonstrate the effectiveness of the N-hydroxy alkyl polyamines methylene phosphonic acids in chelating $Fe^{+2}$, the following test procedure was utilized. Into a flask that contained a known concentration of the sequestering agent, and enough sodium hydroxide or hydrochloric acid to give the desired pH was placed a 100 ml. aqueous sample of ferrous ammonium sulfate (20 ppm of $Fe^{+2}$) after final pH adjustment the solution was allowed to remain at ambient temperatures for 48 hours. The solution was centrifuged for one hour to remove collodial iron hydroxide and an aliquot of the supernatant solution was analyzed by atomic absorption to determine the iron concentration.

The following table illustrates the ability of the sequestering agents of the present invention to sequester $Fe^{+2}$, as compared to the well known sequestering agent tetrasodium ethylenediamine tetra-acetate (EDTA).

TABLE III

| pH | Sequestering Agent (ppm) Product Example | | Amount of iron Sequestered (ppm) |
|---|---|---|---|
| 5 | 1 | (50) | (19) |
| 5 | 2 | (50) | (19) |
| 5 | 3 | (50) | (18) |
| 5 | EDTA | (50) | ( 7) |
| 7 | 1 | (50) | (19) |
| 7 | 2 | (50) | (17) |
| 7 | 3 | (50) | (11) |
| 7 | EDTA | (50) | ( 7) |
| 10 | 1 | (150) | (17) |
| 10 | 2 | (150) | ( 8) |
| 10 | 3 | (150) | (20) |
| 10 | EDTA | (150) | ( 6) |

As one can observe from the preceding table the sequestering agents of this invention are as effective, and in some cases superior, to EDTA when tested over a wide pH range.

The sequestering agents of this invention are also quite effective in sequestering other metal cations in aqueous solutions. For example, a test was conducted in which 60 ppm of the sequesterant were dissolved in 100 ml. of water. The pH was adjusted to 9 and maintained there. Metal cations were added, in the following amounts, before a noticeable precipitate was formed.

TABLE IV

| Sequesterant Product | Metal (ppm) Sequestered per 60 ppm of Sequesterant | |
| --- | --- | --- |
| Example 1 | Fe$^{+3}$ | (60) |
| Example 1 | Al$^{+3}$ | (120) |
| Example 1 | Cu$^{+2}$ | (120) |
| Example 1 | Ni$^{+2}$ | (50) |
| Example 3 | Fe$^{+3}$ | (60) |
| Example 3 | Al$^{+3}$ | (120) |
| Example 3 | Cu$^{+2}$ | (120) |
| Example 3 | Ni$^{+3}$ | (60) |

Other heavy metals sequestered by the sequestering agents of this invention such as cobalt, manganeses, chromium and the like.

In summary, the products of this invention are oxyalkylated, phosphomethylolated polyalkylene polyamines having at least three amino units. Oxyalkylation is preferably carried out with ethylene oxide, propylene oxide or butylene oxide, most preferably with ethylene oxide. In the preferred embodiment, only one alkylene oxide is added per nitrogen-bonded hydrogen, i.e. —N—AOH are specifically —N—CH$_2$CH$_2$OH. The phosphomethylolated groups, i.e.

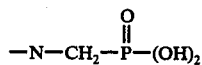

(or salts thereof) preferably comprise at least 50% of the available nitrogen-bonded hydrogens on the polyamine, the remaining nitrogen-bonded hydrogens being preferably nitrogen-bonded hydroxyalkyl groups. The preferred polyalkylene polyamine has 2 – 25 such as 2 – 10 nitrogen units and most preferably 2 – 5 nitrogen units — the preferred embodiment being polyethylene polyamines. These compositions are employed as scale inhibitors, chelating agents, and the like. Various modifications will be evident to those skilled in the art.

The terms "phosphonic acid" and "phosphorous acid" may be used interchangeably and relate to H$_3$PO$_3$, i.e.

Having thus described my invention, what I claim as new and desire by Letters Patent is

1. Process of chelating or inhibiting scale formation in aqueous systems containing metal salts which comprises adding to said aqueous system a small but effective amount of methylene phosphonates of oxyalkylated polyalkylene polyamines having at least 3 nitrogen atoms, said methylene phosphonates having nitrogen-bonded methylene phosphonate units of the formula —CH$_2$PO(OM)$_2$, M being alkali metal, alkaline earth metal, hydrogen, alkyl ammonium or ammonium, wherein as least 50% of the nitrogen-bonded hydrogens of the polyamine are replaced with the methylene phosphonate units and the remainder of the nitrogen-bonded hydrogens are oxyethylated.

2. The process of claim 1 where the methylene phosphonates of oxyalkylated polyalkylene polyamines have the formula

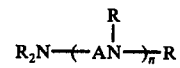

where the Rs are —A'—OH or —CH$_2$PO(OM)$_2$,

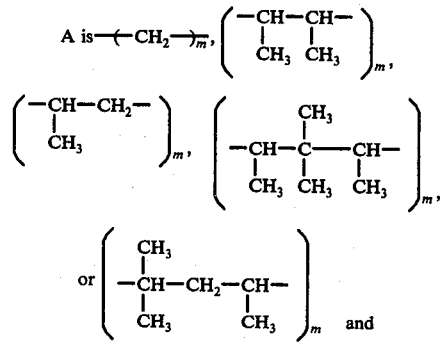

m is 2–10,
n is 2–25, and
A'—OH is Et—OH, Pr—OH, Bu—OH or mixtures thereof and Et is ethylene, Pr is propylene and Bu is butylene.

3. The process of claim 2 where A in the methylene phosphonates of oxyalkylated polyalkylene polyamines is —CH$_2$CH$_2$.

4. The process of claim 3 where A'—OH in the methylene phosphonates of oxyalkylated polyalkylene polyamines is Et—OH.

5. The process of claim 1 where the methylene phosphonate of an oxyalkylated polyalkylene polyamine is present in an amount of at least 0.1 part per million of aqueous system.

6. The process of claim 5 where the methylene phosphonate of an oxyalkylated polyalkylene polyamine is present in an amount of from 0.1 to 100 p.p.m of aqueous system.

7. The process of claim 5 where the methylene phosphonate of an oxyalkylated polyalkylene polyamine is present in an amount of from 50 p.p.m. to 50,000 p.p.m. of aqueous system.

8. The process of claim 1 where M is hydrogen.

9. The process of claim 1 where M is sodium.

* * * * *